US007892288B2

(12) United States Patent
Blaylock et al.

(10) Patent No.: US 7,892,288 B2
(45) Date of Patent: Feb. 22, 2011

(54) FEMORAL AUGMENTS FOR USE WITH KNEE JOINT PROSTHESIS

(75) Inventors: Jeff Blaylock, Fort Wayne, IN (US); Michael Cook, Claypool, IN (US); Ron Donkers, Warsaw, IN (US); Scott Dykema, Warsaw, IN (US); Maleata Hall, Warsaw, IN (US); John Meyers, Columbia City, IN (US); Arlen D. Hanssen, Rochester, MN (US); David G. Lewallen, Rochester, MN (US)

(73) Assignee: Zimmer Technology, Inc., Warsaw, IN (US)

( * ) Notice: Subject to any disclaimer, the term of this patent is extended or adjusted under 35 U.S.C. 154(b) by 563 days.

(21) Appl. No.: 10/794,721

(22) Filed: Mar. 5, 2004

(65) Prior Publication Data

US 2004/0172137 A1   Sep. 2, 2004

Related U.S. Application Data

(63) Continuation-in-part of application No. 10/225,774, filed on Aug. 22, 2002, now abandoned.

(60) Provisional application No. 60/315,148, filed on Aug. 27, 2001.

(51) Int. Cl.
    *A61F 2/38* (2006.01)
(52) U.S. Cl. ............... 623/20.15; 623/20.36; 623/22.42
(58) Field of Classification Search ............. 623/20.15, 623/20.36, 22.42, 23.21, 23.46
    See application file for complete search history.

(56) References Cited

U.S. PATENT DOCUMENTS 2,947,308 A * 8/1960 Gorman ................... 623/22.35

4,216,549 A * 8/1980 Hillberry et al. ......... 623/20.26

(Continued)

FOREIGN PATENT DOCUMENTS

EP    1 004 283    5/2000

(Continued)

OTHER PUBLICATIONS

The Japanese office action mailed May 26, 2009, in related Japanese Patent Application No. 2004-216179.

(Continued)

*Primary Examiner*—Paul Prebilic
(74) *Attorney, Agent, or Firm*—Baker & Daniels LLP (57) ABSTRACT

A femoral augment, or set of augments, for use with a knee joint prosthesis, where the femoral augment includes a main body portion, an aperture formed within the main body portion and extending in a generally distal/proximal direction, and a pair of legs extending outwardly from said main body portion in a generally posterior direction. In the preferred embodiment, the aperture is configured to receive a stem extension implant, and to allow it to pass through. Additionally, the legs of the femoral augment are preferably configured to be seated proximal of a proximal side of a pair of condylar portions of a femoral component of a knee joint prosthesis. The present invention is intended for situations in which the distal portion of the femur is defective, and it provides a method and devices that allow for preservation of healthy peripheral bone, while still providing the necessary augmentation to the distal portion of the femur.

8 Claims, 9 Drawing Sheets

U.S. PATENT DOCUMENTS

| | | | | |
|---|---|---|---|---|
| 4,659,331 | A * | 4/1987 | Matthews et al. | 623/20.21 |
| 4,711,639 | A * | 12/1987 | Grundei | 623/20.33 |
| 4,883,488 | A * | 11/1989 | Bloebaum et al. | 623/20.34 |
| 4,888,021 | A * | 12/1989 | Forte et al. | 623/20.19 |
| 4,950,298 | A | 8/1990 | Gustilo et al. | |
| 5,163,966 | A * | 11/1992 | Norton et al. | 623/65 |
| 5,197,488 | A * | 3/1993 | Kovacevic | 600/595 |
| 5,226,915 | A * | 7/1993 | Bertin | 623/20.15 |
| 5,358,527 | A * | 10/1994 | Forte | 623/20.27 |
| 5,358,530 | A * | 10/1994 | Hodorek | 623/20.29 |
| 5,549,685 | A * | 8/1996 | Hayes | 623/20.16 |
| 5,782,925 | A * | 7/1998 | Collazo et al. | 623/20.28 |
| 5,871,548 | A * | 2/1999 | Sanders et al. | 623/22.36 |
| 6,074,424 | A | 6/2000 | Perrone et al. | |
| 6,136,029 | A * | 10/2000 | Johnson et al. | 623/16.11 |
| 6,290,725 | B1 * | 9/2001 | Weiss et al. | 623/20.12 |
| 6,423,096 | B1 | 7/2002 | Musset et al. | |
| 6,613,092 | B1 | 9/2003 | Kana et al. | |
| 7,105,026 | B2 | 9/2006 | Johnson et al. | |
| 7,179,295 | B2 * | 2/2007 | Kovacevic | 623/17.15 |
| 2003/0065397 | A1 * | 4/2003 | Hanssen et al. | 623/20.32 |
| 2004/0034432 | A1 * | 2/2004 | Hughes et al. | 623/20.28 |
| 2004/0117024 | A1 * | 6/2004 | Gerbec et al. | 623/18.11 |
| 2004/0162619 | A1 | 8/2004 | Blaylock et al. | |
| 2004/0172137 | A1 | 9/2004 | Blaylock et al. | |
| 2005/0278034 | A1 | 12/2005 | Johnson et al. | |
| 2007/0088443 | A1 | 4/2007 | Hanssen et al. | |

FOREIGN PATENT DOCUMENTS

| | | |
|---|---|---|
| FR | 2772593 A1 * | 6/1999 |
| JP | 2001-503283 A | 3/2001 |
| WO | WO97-30661 A1 | 8/1997 |
| WO | WO99/32053 A1 | 1/1999 |
| WO | WO 02/05732 A1 * | 1/2002 |

OTHER PUBLICATIONS

The European Search Report mailed Jun. 22, 2005 in related European patent application No. 04254352.0.

The Canadian Office Action mailed Mar. 12, 2010 in related Canadian Application No. 2,473,633.

The Australian Office Action mailed Jan. 13, 2010 in related Australian Application No. 2004203348.

* cited by examiner

FEMORAL AUGMENTS FOR USE WITH KNEE JOINT PROSTHESIS

This application is a continuation-in-part of prior application Ser. No. 10/225,774, filed Aug. 22, 2002, (now abandoned) which claims the benefit of Provisional Application No. 60/315,148, filed Aug. 27, 2001, both of which are hereby incorporated by reference.

The present invention relates generally to a bone augmenting member used to reinforce damaged bone, and more particularly to an augment for the distal portion of a human femur, where the augment is intended to be implanted in the distal portion of the femur, just proximal of the femoral portion of a knee joint prosthesis. Thus, the present invention relates to a void-filling component used to aid in the reconstruction of distal femurs that have undergone significant bone loss. In addition, the invention also relates to a provisional augment used temporarily to ensure that the permanent augment will be seated within the bone correctly, as well as to a tool used for removing the provisional augment.

BACKGROUND OF THE INVENTION

Knee replacement surgery methods and knee joint prostheses are known in the art. A typical knee joint prosthesis includes a rounded femoral component that is attached to the distal portion of the femur, and a tibial component (which may be formed of a single piece or from two separate pieces that are joined together) that is attached to the proximal portion of the tibia. The femoral component rides on the exposed surface of the tibial component, replicating knee movement. When such knee replacement surgery is performed, an incision is made to expose the knee joint in order to enable removal of both the proximal portion of the tibia and the distal portion of the femur, which creates surfaces upon which the tibial and femoral components of the knee prosthesis can be attached.

In certain situations, additional portions of the femur, other than the relatively narrow distal portion being removed during knee replacement surgery, may also be damaged by, for example, loss of bone from prior procedures. In such situations, a relatively thick distal portion of the femur is often removed, and it is replaced with an augment block or a wedge-shaped augment shaped like the bone that has been removed. However, such previously known methods often result in the removal of an unnecessary amount of healthy bone along with the damaged bone. Thus, for example, even in cases where the peripheral bone was healthy, and only the internal bone was damaged, prior art methods often removed both the healthy peripheral bone and the damaged internal bone.

BRIEF SUMMARY OF THE INVENTION

The present invention is intended for situations in which the distal portion of the femur is defective, and it provides a method and devices that allow for preservation of healthy peripheral bone, while still providing the necessary augmentation to the distal portion of the femur. Preservation of the healthy peripheral bone provides for early onset of bony ingrowth into the femoral augment and allows the bone to infiltrate the augment, restoring the bony platform upon which other implants can reside. Preservation of the peripheral bone also allows for maintenance of soft tissue attachment to the outside of the femur.

More specifically, the present invention provides a femoral augment for use with a knee joint prosthesis, where the femoral augment includes a main body portion, an aperture formed within the main body portion and extending in a generally distal/proximal direction, and a pair of legs extending outwardly from said main body portion in a generally posterior direction. In the preferred embodiment, the aperture is configured to receive a stem extension implant. Additionally, the legs of the femoral augment are preferably configured to be seated proximal of a proximal side of a pair of condylar portions of a femoral component of a knee joint prosthesis.

In the preferred form of the present invention, multiple sizes of femoral augment will be available, with multiple distal/proximal heights being provided for at least some of the different sizes. The lower height, or shorter, femoral augments preferably each include proximal sides of the main body portion that each define a relatively flat surface with a generally trapezoidal shape, where the trapezoidal shape is defined by a longer base section and a shorter base section that are connected by two leg sections. The greater height, or taller, femoral augments preferably each include outer medial and lateral surfaces of their main body portions that are tapered inwardly towards a proximal direction, thereby defining (for each augment) a generally conical portion of a generally quadrilateral-shaped cross-section with a truncated proximal surface.

The present invention also relates to an implant system for use with a knee joint prosthesis, where the system includes at least one femoral component of a knee joint prosthesis and at least one femoral augment configured to be seated proximal of the at least one femoral component. In the preferred form, each femoral augment includes a main body portion and a pair of legs extending outwardly from the main body portion in a generally posterior direction. The legs are preferably configured to be seated proximal of a proximal side of a pair of condylar portions found on the femoral component. The system may also include a pusher that is configured and arranged for implanting one of the femoral augments into a distal portion of a femur; and at least one provisional femoral augment that corresponds in shape, size and height to the at least one femoral augment. Where multiple femoral augments of different shapes, sizes and heights are provided, multiple provisionals will also be provided, with one provisional corresponding to each different size, shape and height of femoral augment. The system may also include a provisional remover that is configured to cooperate with a groove located on each provisional, where the provisional remover is used to remove the provisional femoral augment from an implanted position. Preferably, at least one of the multiple femoral augments of different shapes, sizes and heights is configured to cooperate with multiple femoral components of different sizes.

Another aspect of the present invention relates to a set of femoral augments for use with a knee joint prosthesis, where the set includes a plurality of femoral augments of a plurality of different sizes. The plurality of different sizes can include variations in the medial/lateral dimensions and/or variations in the anterior/posterior dimensions. Preferably the set of femoral augments also includes femoral augments of a plurality of different distal/proximal heights in at least one of the sizes.

Throughout this application various positional terms—such as distal, proximal, medial, lateral, anterior and posterior—will be used in the customary manner when referring to the human anatomy. More specifically, "distal" refers to the area away from the point of attachment to the body, while "proximal" refers to the area near the point of attachment the body. For example, the proximal femur refers to the portion of the femur near the hip, while the distal femur refers to the portion of the femur near the tibia. The terms "medial" and "lateral" are also essentially opposites, where "medial" refers to something situated closer to the middle of the body, while "lateral" refers to something situated closer to the left side or the right side of the body (than to the middle of the body). Finally, with regard to anterior and posterior, "anterior" refers to something situated closer to the front of the body and "posterior" refers to something situated closer to the rear of the body.

BRIEF DESCRIPTION OF THE DRAWINGS

Preferred embodiments of the present invention are described herein with reference to the drawings wherein.

DETAILED DESCRIPTION OF THE INVENTION

Figure 1:
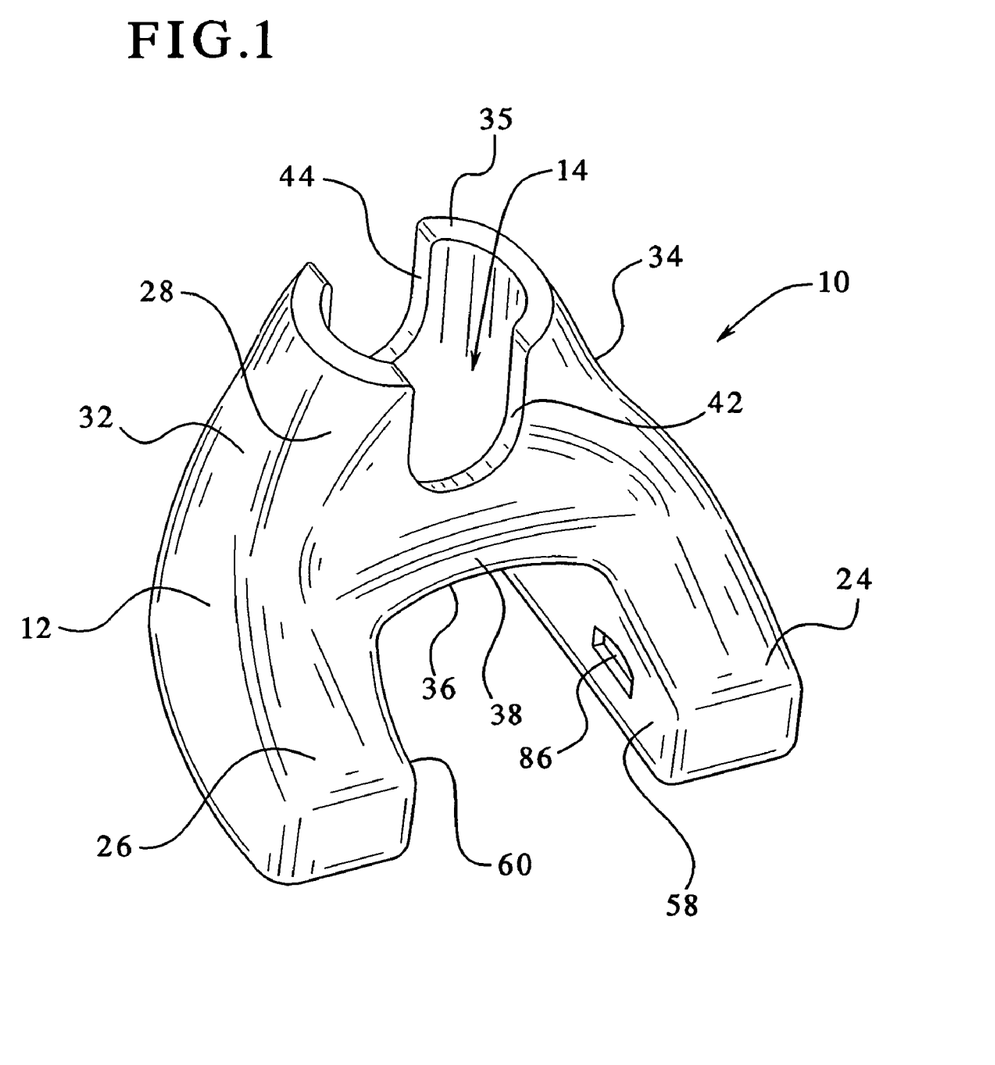
FIG. 1 is a posterior perspective view of one example of a femoral augment of the present invention.

Referring to FIG. 1, one example of a femoral augment of the present is shown, and is designated as femoral augment 10. Femoral augment 10 is preferably made from a tantalum based porous material, such as Trabecular Metal™, or it may be made from another metal that is coated with a tantalum-based porous metal or other porous coating. Trabecular Metal™ is desirable because it resembles bone and approximates the physical and mechanical properties of bone better than most other materials. Use of such a metal enables increased bonding with the adjacent bone by allowing the bone to grow into its highly porous surface. Although solid Trabecular Metal™ or a Trabecular Metal™ coating is preferred, the femoral augments of the present invention may also be made of other materials, but they are preferably made of a material that facilitates bony ingrowth.

The femoral augment of the present invention is anatomically sized and shaped to correspond to the internal size and shape of a distal human femur and to fill an existing cavitary defect within the distal human femur, preferably with only minor shaping of the cavitary defect being required. In the preferred embodiment, a system of different stock sizes of augments would be available, as discussed more fully below, with different sizes being used for filling different sized defects in different sized femurs. Further, each of the different sizes of femoral augments is preferably available in a variety of heights (measured in the distal/proximal direction). For example, the heights could range from approximately 20 mm to approximately 50 mm (of course other heights are also contemplated as being within the scope of the invention). By providing femoral augments of different sizes, with different heights available for each of the sizes, the optimal size and height augment can be selected so that only a minimal amount of healthy bone needs to be removed, which promotes the early onset of bony in-growth. Additionally, the configuration of the femoral augments, as well as the availability of various sizes and heights, allows for the preservation of a significant amount of peripheral bone, whereby such bone can later grow to infiltrate the augment and the femoral component of the implant to restore the bony platform upon which the augment and the implant reside.

Turning first to femoral augment 10 of FIGS. 1-4, where femoral augment 10 is one example of an augment with a relatively large height (such as in the approximately 50 mm range), the various features of this augment will be described. Augment 10 includes a main body portion 12, with an aperture 14 formed therein that extends generally in a distal/proximal direction. Extending outwardly from main body portion 12, in a generally posterior direction, are a pair of legs 24/26.

The main body portion 12 of femoral augment 10 includes a tapered outer lateral surface 32 and a tapered outer medial surface 34 that are each tapered inwardly towards the proximal direction to define a generally conical portion, of a generally quadrilateral-shaped horizontal cross-section, with a truncated proximal surface 35. The FIG. 1 example of femoral augment 10 is configured for use within a left femur, and therefore the designations such as lateral and medial relate to such an intended implantation location. The outer lateral surface 32 preferably tapers at a greater slope (i.e., is closer to 90° with respect the horizontal) than the taper of the outer medial surface 34, which corresponds to the configuration of the distal portion of the human femur. Thus, due to the different lateral and medial tapers, at least the proximal portion 28 of the main body portion 12 of the femoral augment 10 is asymmetric with respect to its lateral and medial sides. However, the more distal portion 38 of the main body portion 12 (i.e., the portion closer to web portion 36) is preferably symmetric, with respect to its lateral and medial sides, because the corresponding portion of the human femur is more symmetric in this area.

A femoral augment of the size and height of the FIG. 1 embodiment, but which is instead intended for use within a right femur, would simply be a mirror image of that shown in FIG. 1. However, since the designations "lateral" and "medial" are reversed for the right augment, the outer lateral surface 32 will still be the surface that preferably tapers at a greater slope (i.e., is closer to 90°) than the taper of the outer medial surface. Further, because of the symmetric distal portion 38, femoral augments of shorter heights that lack the asymmetric proximal portion 28 need not be produced specifically as right side augments or left side augments. Instead, as described more fully below when discussing the shorter augments of FIGS. 6 and 7, a single augment configuration could be used within either the right femur or within the left femur because the entire augment is preferably symmetric with respect to the lateral and medial sides.

In the embodiment of FIG. 1, femoral augment 10 preferably also includes two cutout portions 42 and 44, with cutout portion 42 being provided in the proximal area of the posterior side and cutout portion 44 being provided in the proximal area of the anterior side. If cutout portions 42 and 44 are not provided, the wall thickness of this portion of the augment, as dictated by the internal shape of the distal portion of the femur, may be too thin to be stable. Thus, instead of risking breakage of such a thin portion at this area, cutout portions 42 and 44 are created. However, if a particular configuration of femoral augment enables sufficient wall thickness in this area, one or both of the cutout portions may be omitted.

Figure 2:
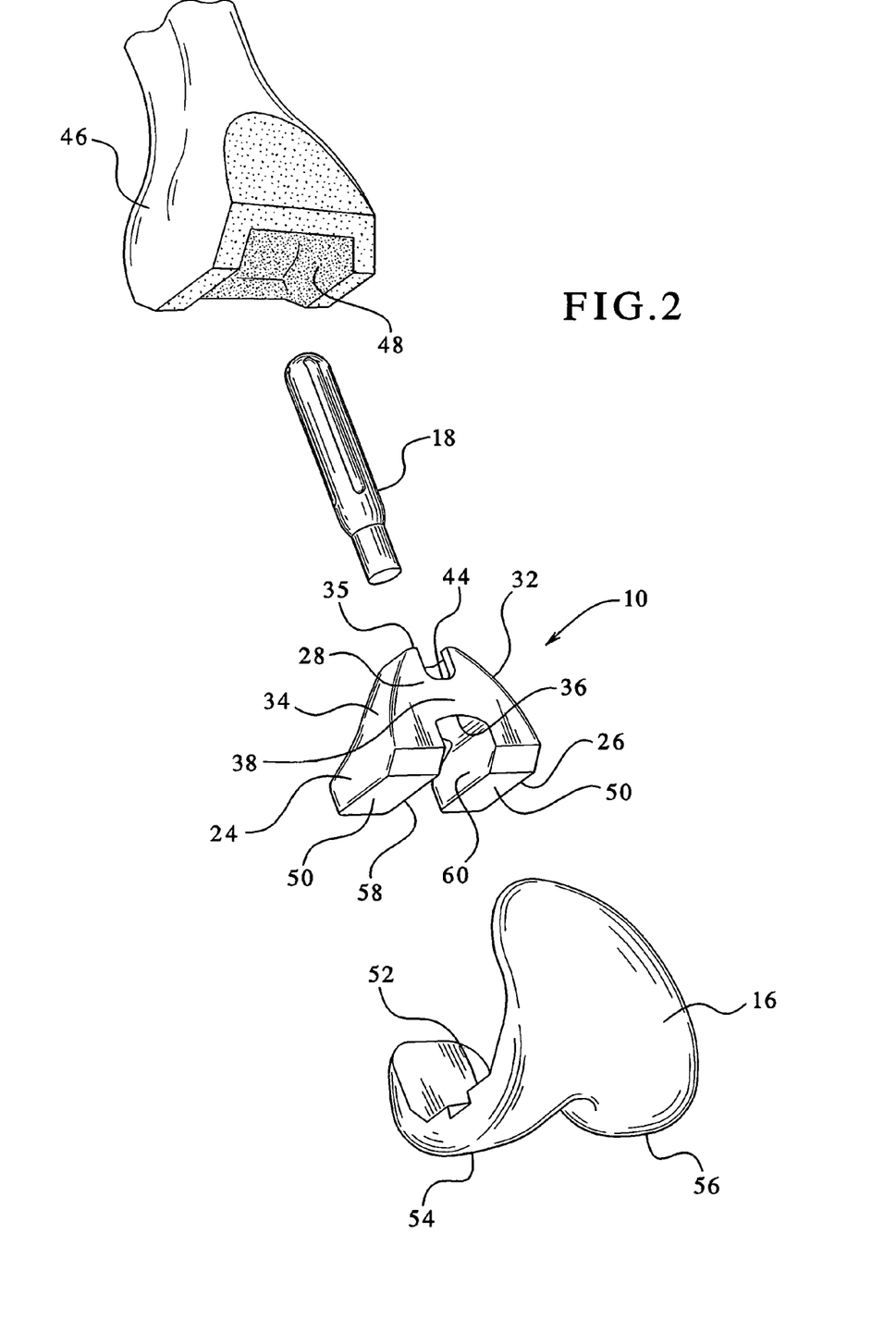
FIG. 2 is an exploded anterior perspective view of one example of a femoral augment of the present invention, shown with a femur and a femoral component of a knee joint prosthesis.

Turning now to FIG. 2, this figure shows an exploded view of the environment within which the femoral augment of the present invention will be used. In particular, FIG. 2 shows an anterior view of a femoral component 16 of a knee joint prosthesis, the femoral augment 10, a stem extension implant 18 and a left femur 46. Femur 46 has been resected to accept femoral component 16. Additionally, a cavity 48 for receiving the augment 10 has been prepared within the distal portion of the femur 46. Preparation of cavity 48 should only involve slight shaping of an existing cavitary defect so that the existing cavitary defect better conforms to the shape of the femoral augment being implanted. Such shaping can be performed using, for example, a burr tool or a rasp. As can be seen in FIG. 2, cavity 48 does not extend to the peripheral portions of femur 46. Accordingly, the peripheral portions of the bone, if healthy, are preserved. In use, femoral augment 10 is implanted into cavity 48, and the femoral component 16, with the stem extension 18 attached thereto, is then implanted into the femur using any desired implantation technique. Preferably, the femoral augment 10 is affixed to the femoral component 16 by a layer of bone cement.

Figure 3:
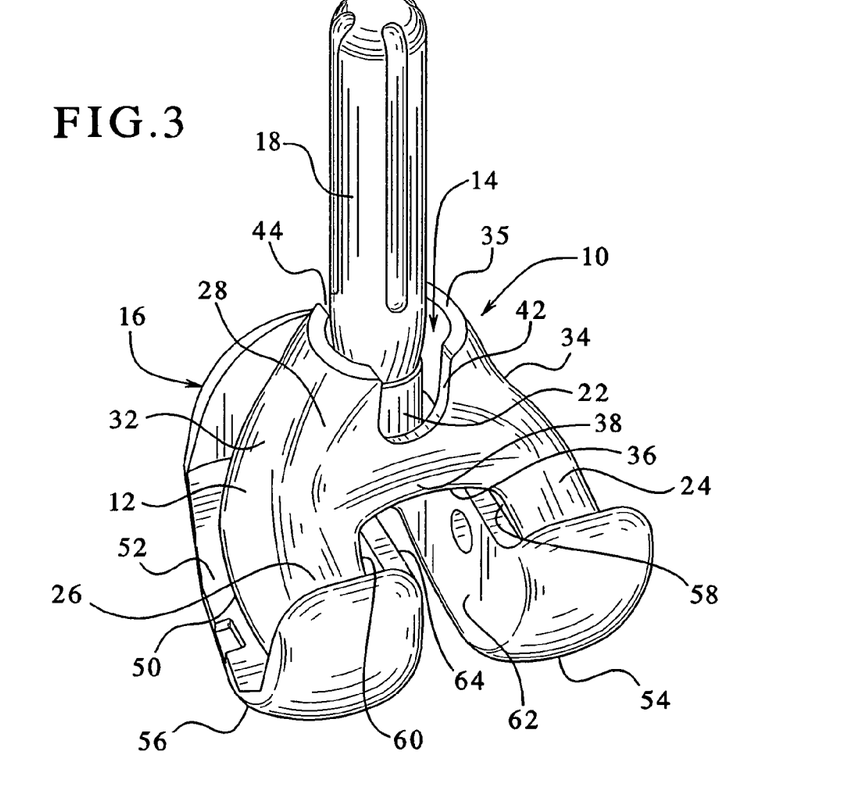
FIG. 3 is a posterior perspective view of the femoral component of FIG. 1, shown with a femoral component and a stem extension.

The femoral augments of the present invention can be configured to be used with a variety of different designs of femoral components, with femoral component 16 shown in FIGS. 2 and 3 being just one example of such a component. For example, the present femoral augments shown and described herein can be used with the LCCK and Rotating Hinge Knee femoral components from the NexGen® Complete Knee Solution, manufactured by Zimmer Inc. of Warsaw, Ind. However, although only one example of a femoral component is shown and described herein, one of ordinary skill in the art would be able to modify, if necessary, the femoral augments described herein to be used in association with other femoral component designs.

Turning now to FIG. 3, femoral augment 10 is shown positioned proximal of femoral component 16. In the preferred embodiment, there is preferably a slight amount of space between the distal side 50 of the legs 24/26 of femoral augment 10 and the proximal side 52 of the convex condylar portions 54 and 56 of the femoral component 16. In the preferred embodiment, this space is between approximately 5 mm and approximately 10 mm, although spaces of different sizes may also be provided, if desired. This space provides the surgeon with some flexibility with regard to the placement of the femoral augment 10 relative to the femoral component 16. For example, conventional distal augments (not shown) could be positioned on the proximal side(s) 52 of either, or both, condylar portions 54 and/or 56 in order to compensate for cortical bone loss in the distal femur. Depending on the configuration of the femoral component, the surgeon can include up to a 5 mm distal augment (such as when used with a NexGen® LCCK femoral component) or up to a 10 mm distal augment (such as when used with a NexGen® Rotating Hinge Knee femoral component). Moreover, the space may also allow for the femoral augments to be used with other configurations of femoral components, without the need to modify either the femoral augments or the femoral components.

As can be seen in FIG. 3, certain portions of the femoral augment 10 are configured to accept certain portions of the femoral component of a knee joint prosthesis. For example, aperture 14 is configured to receive the stem extension implant 18, and to allow it to pass through. As known in the art, stem extension implants, such as stem extension 18, are commonly attached to the stem bases of femoral components (such as stem base 22 of femoral component 16) in order to more securely seat the femoral component within the femur. Additionally, the web portion 36 and the inner leg surfaces 58 and 60 (best seen in FIG. 1) define a recessed portion configured to accommodate inner rails 62 and 64, which extend in the generally proximal direction from the proximal side 52 of condylar portions 54 and 56 of the femoral component 16. Of course, if rails 62 and 64 are omitted from femoral component 16, or are reduced in height, the recessed portion of the femoral augment 10 may be omitted, or reduced in height, accordingly.

As mentioned earlier, femoral augment 10 is preferably used to fill a void within a distal femur. In many situations, the defective bone being removed will not be balanced with respect to the intended implanted location of the stem extension 18. In such situations, the femoral augment 10 can be offset (i.e., rotated), in either direction, with respect to the femoral implant. The availability of using femoral augment 10 in a variety of different offset positions allows for the location of the augment to better correspond to the location of the defective bone that has decayed or been removed, thereby providing another way of reducing the need to remove healthy bone in order to accommodate the augment. Additionally, allowing placement of the femoral augment that is somewhat independent of the location of the femoral component enables the surgeon to maximize contact between the femoral augment and the remaining endosteal bone of the distal femur.

Figure 4:
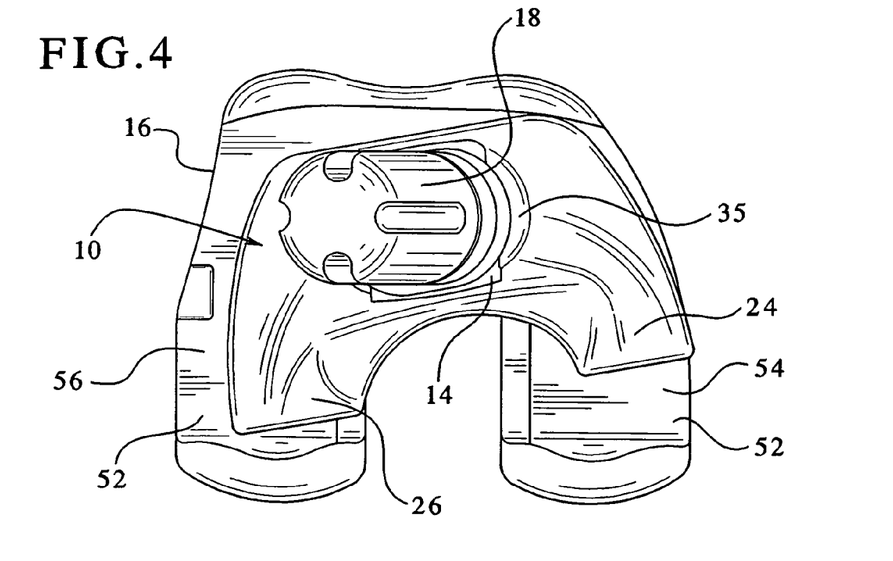
FIG. 4 is a proximal perspective view of the femoral component of FIG. 1, shown rotated with respect to the femoral component.

One example of such offset positioning is shown in FIG. 4, which includes an offset of approximately 10° between femoral augment 10 and femoral component 16. The preferred embodiment may be offset up to the approximately 10° shown in FIG. 4. However, it is contemplated that different offset amounts may also be provided, if necessary, with minor modifications to the augment and/or to the femoral component.

In addition to allowing offset positioning, the present femoral augment may also be positioned in a "tilted" orientation, with respect to the femoral component (i.e., where such tilting involves raising or lowering the lateral, medial, anterior or posterior sides a slight amount). In order to facilitate such tilted positioning, with respect to raising or lowering the lateral or medial sides, the inner surfaces of the legs are sloped so that such tilting is not hindered by the rails of the femoral component. More specifically, as can be seen in FIG. 3, inner leg surfaces 58 and 60 are sloped inwardly, towards each other, when going from their distal portions to their proximal portions in order to allow either medial or lateral tilting, without interference from rails 62 and 64. Accordingly, the recessed portion between legs 24 and 26 is narrowest near a proximal portion thereof and widest near a distal end. Of course, aperture 14 also provides sufficient clearance with respect to stem extension 18 so that tilting of the augment 10 with respect to the femoral component 16 is not hindered at this area either.

Figure 5:
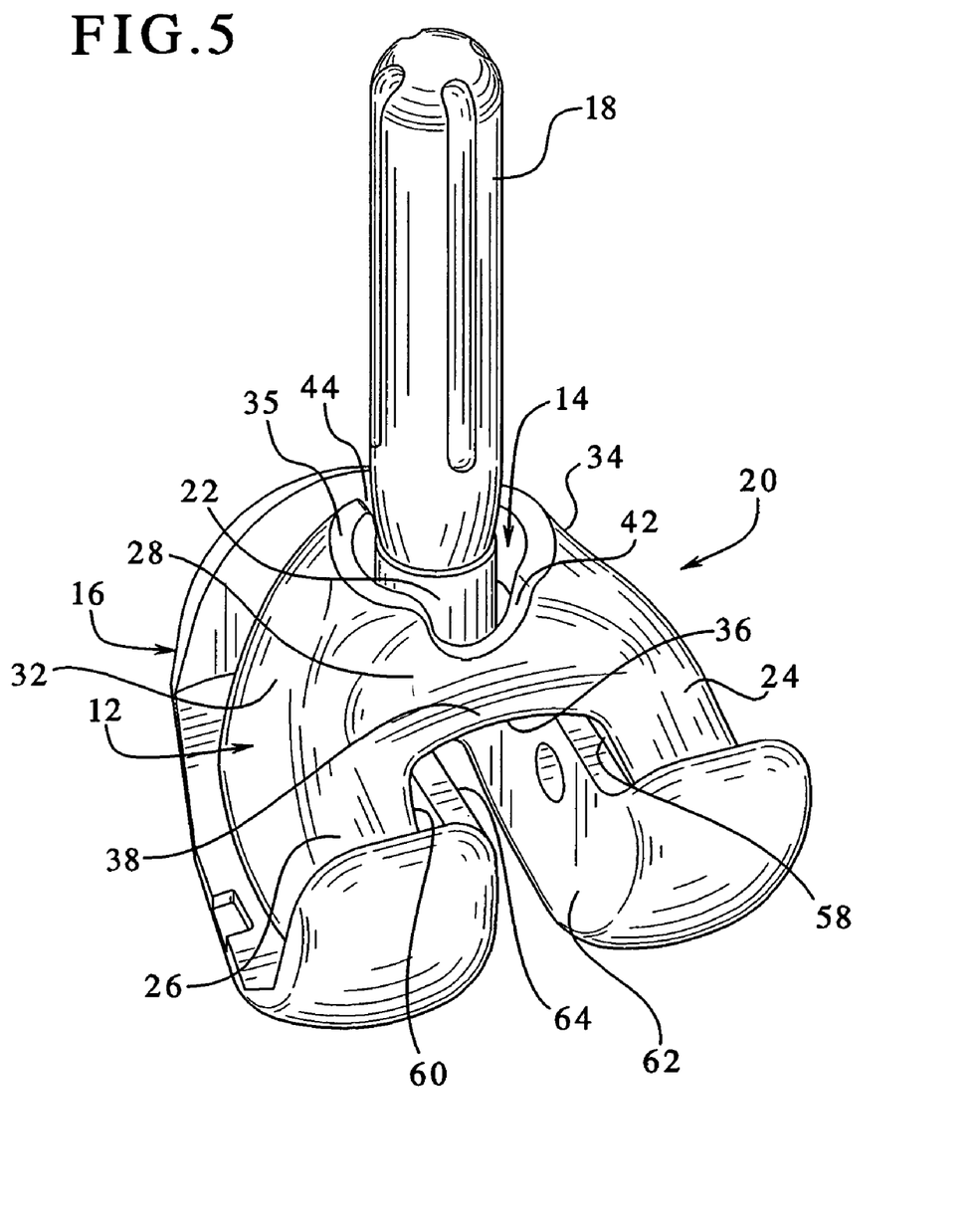
FIG. 5 is a posterior perspective view of a femoral component of a different height than that shown in FIG. 3, shown with a femoral component and stem extension.
Figure 6:
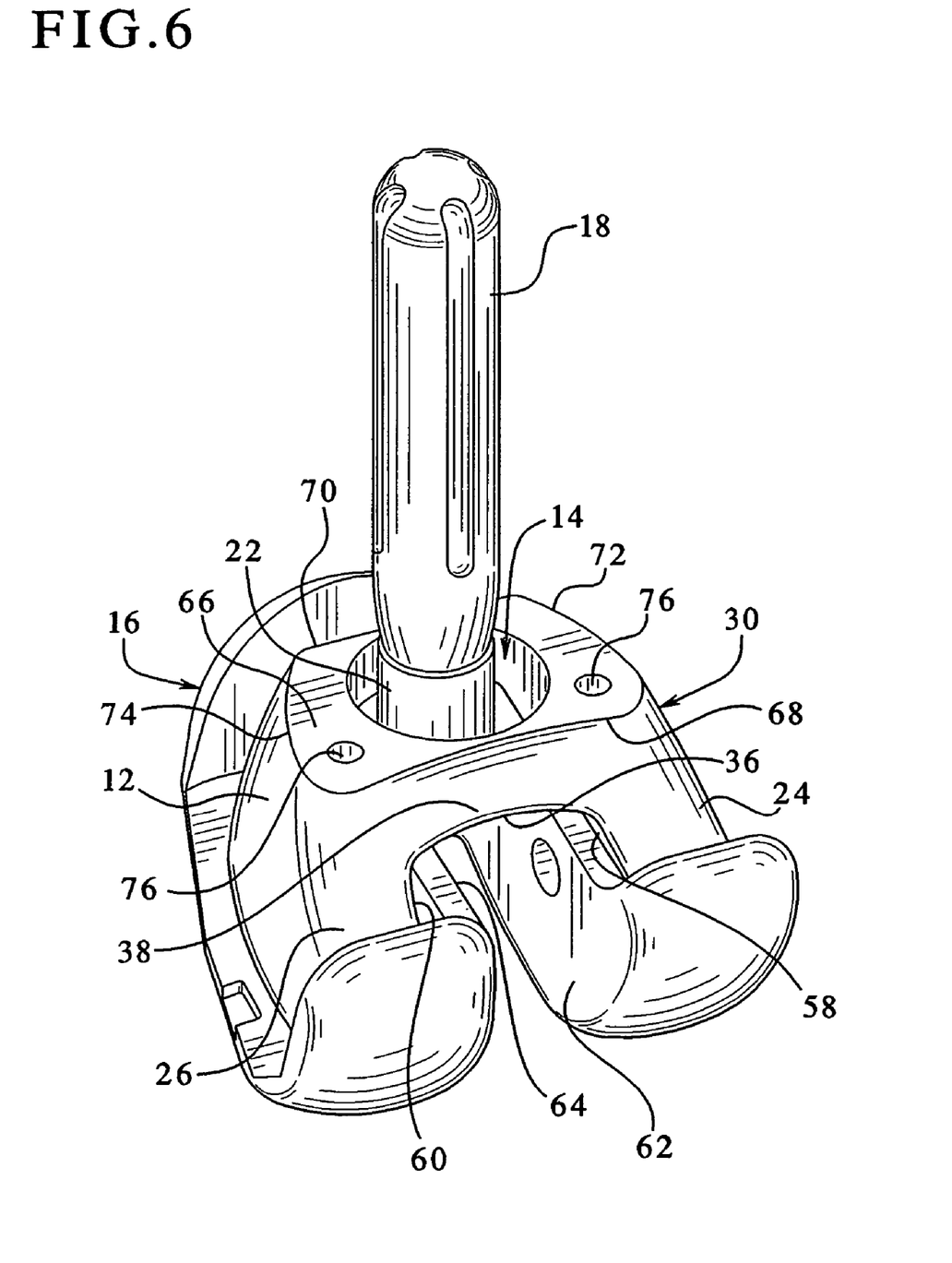
FIG. 6 is a posterior perspective view of a femoral component of a lesser height that that shown in FIG. 5, shown with a femoral component and stem extension.
Figure 7:
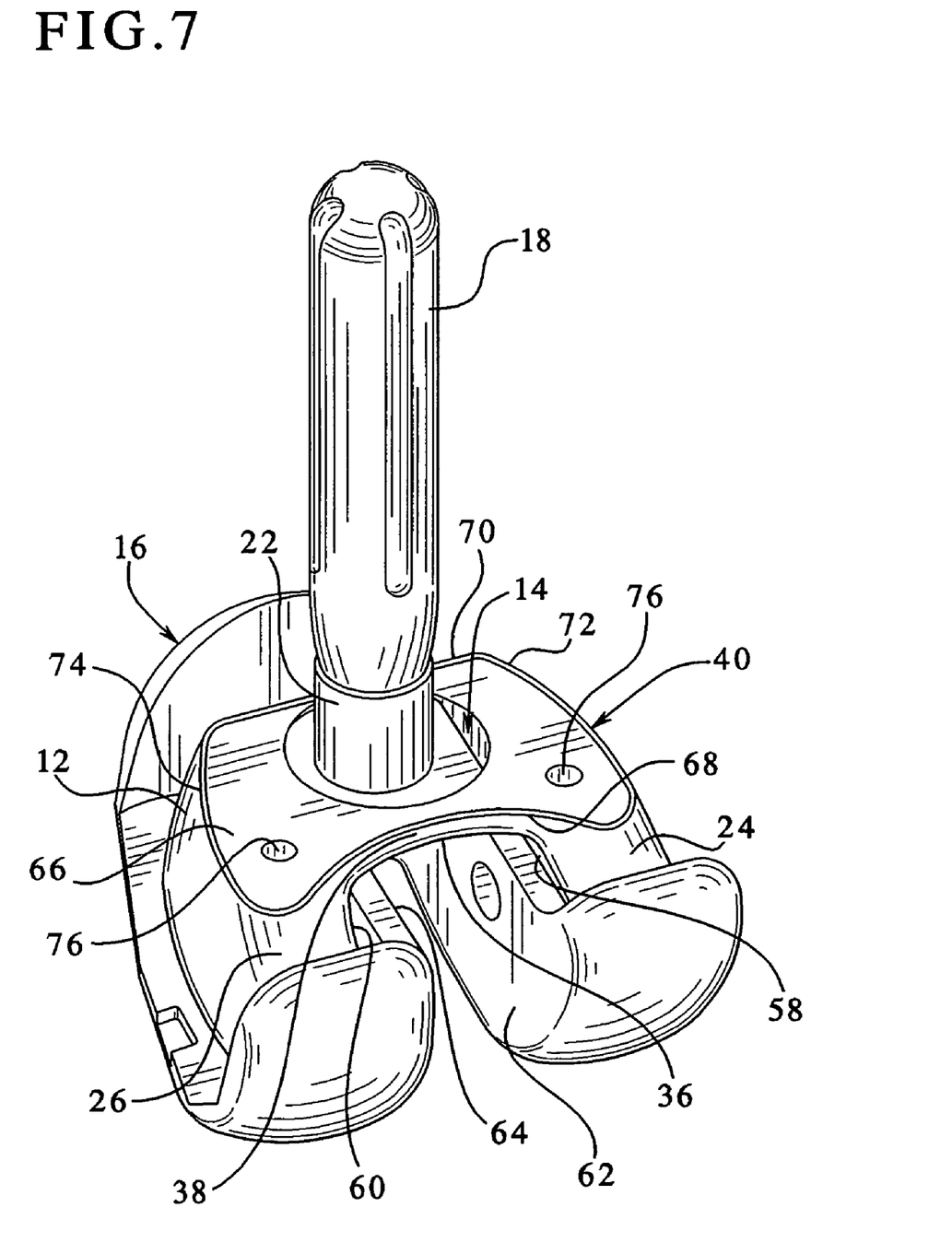
FIG. 7 is a posterior perspective view of a femoral component of a different height that that shown in FIG. 6, shown with a femoral component and stem extension.

The femoral augment 10 shown in FIGS. 1-4 is one example of a femoral augment with a relatively large distal/proximal dimension (i.e., a relatively tall height, such as 50 mm). FIGS. 5, 6 and 7 show examples of femoral augments of different heights (shown with the same femoral component 16 of FIGS. 2 through 4), but of the same size as augment 10 of FIG. 1. More specifically, FIG. 5 shows femoral augment 20, which is slightly shorter than augment 10 of FIG. 1; FIG. 6 shows femoral augment 30, which is slightly shorter than augment 20 of FIG. 5; and FIG. 7 shows femoral augment 40, which is slightly shorter than augment 30 of FIG. 6. Femoral augments 10, 20, 30 and 40 (of FIGS. 1, 5, 6 and 7) are all essentially the same size with respect to the anterior/posterior dimensions and the medial/lateral dimensions. However, the distal/proximal dimensions (heights) of augments 20, 30 and 40 are reduced, when compared to augment 10 of FIG. 1. In other words, augments 20, 30 and 40 are essentially truncated versions of augment 10 (with minor variations), where the truncation plane is located most distal for augment 40, slightly more proximal for augment 30, and still more proximal for augment 20. It is also contemplated that augments 20, 30 and 40 could be exact truncated versions of augment 10.

Turning first to FIG. 5, a first shortened version of an augment is shown and is designated as femoral augment 20. In the preferred embodiment, femoral augment 20 is approximately 40 mm in height (10 mm less than femoral augment 10 of FIG. 1). However, the 40 mm height is only a suggested height, and accordingly, femoral augment 20 may also be produced in another height. Since the preferred embodiments of femoral augment 20, and augments 30 and 40, are essentially truncated versions of femoral augment 10 (with minor variations), many of the same features of augment 10 will be found in augments 20, 30 and 40. Thus, for ease of description, similar features to those of augment 10 will be designated with the same references numbers in the description of augments 20, 30 and 40, and only minimal, if any, additional description of these similar features will be provided.

As with femoral augment 10 of FIGS. 1-4, femoral augment 20 of FIG. 5 includes a main body portion 12, an aperture 14, and legs 24 and 26. Femoral augment 20 also preferably includes cutout portions 42 and 44. Although, as discussed above with regard to femoral augment 10, either, or both, of the cutout portions 42 and 44 may be omitted if sufficient wall thickness can be provided to enable proximal surface 35 to be an annular planer surface. As can be seen from a comparison of FIGS. 3 and 5, cutout portions 42 and 44 of femoral augment 20; of FIG. 5 are not as tall as those of FIG. 3.

Femoral augment 20, like femoral augment 10, also includes asymmetric proximal portion 28 and symmetric distal portion 38, where asymmetric proximal portion 28 defines a generally conical portion, of a generally quadrilateral-shaped cross-section, with a truncated proximal surface 35. Also, on femoral augment 20, the tapered outer lateral surface 32 tapers at a greater slope than the tapered outer medial surface 34, as was the case with femoral augment 10. Accordingly, femoral augment 20 is to be used within a left femur, and a mirror image of femoral augment 20 would be provided for use within a right femur.

Turning now to FIG. 6, a second shortened version is shown and is designated as femoral augment 30. In the preferred embodiment, femoral augment 30 is preferably approximately 30 mm in height (20 mm less than femoral augment 10 of FIG. 1). However, 30 mm is only a suggested height, and, as mentioned earlier with regard to other suggested dimensions provided, femoral augment 30 may be produced in another height.

As with the other femoral augments described (augments 10 and 20), femoral augment 30 includes a main body portion 12, an aperture 14, and legs 24 and 26. However, unlike augments 10 and 20, augment 30 lacks the asymmetric generally conical proximal portion 28, and merely includes the symmetric portion 38 (referred to as the symmetric distal portion 38 in augments 10 and 20). Accordingly, as augment 30 is symmetric with respect to its medial and lateral sides, specific left and right augments of this size need not provided because augment 30 can be used within either the left femur or within the right femur.

Since femoral augment 30 lacks the generally conical proximal portion of augments 10 and 20, it instead includes a substantially flat proximal surface 66, which is generally trapezoidal in shape (albeit somewhat rounded). Trapezoidal proximal surface 66 is defined by longer base section 68, shorter base section 70, and a pair of leg sections 72 and 74, which connect the base sections 68 and 70. In this embodiment, leg sections 72 and 74 are formed by somewhat curved lines, and base sections 68 and 70 are formed by generally straight lines. This embodiment may optionally include one or more visualization holes 76, which are provided to allow the surgeon to view the defective bone into which the augment 30 is being implanted.

Turning now to FIG. 7, a third shortened version is shown and is designated as femoral augment 40. In the preferred embodiment, femoral augment 40 is preferably in the range of approximately 20 to 22 mm in height (18 to 20 mm less than femoral augment 10 of FIG. 1). However, the 20 to 22 mm range is only a suggested height range, and, as mentioned earlier with regard to other suggested dimensions provided, femoral augment 40 may be produced in another height, if desired.

Femoral augment 40, like femoral augment 30, also lacks generally conical proximal portion of augments 10 and 20, but instead also includes a substantially flat proximal surface 66 that is generally trapezoidal in shape (albeit somewhat rounded). As with the FIG. 6 embodiment, the trapezoidal proximal surface 66 of the FIG. 7 embodiment is also defined by longer base section 68, shorter base section 70, and a pair of leg sections 72 and 74, which connect the base sections 68 and 70. In this embodiment also, leg sections 72 and 74 are formed by somewhat curved lines and shorter base section 70 is formed of a generally straight line. However, in the FIG. 7 embodiment, the longer base section 68 is formed by a generally curved line. This embodiment, similar to the FIG. 6 embodiment, may also optionally include one or more visualization holes 76. As with the FIG. 6 embodiment, augment 40 of FIG. 7 is symmetric with respect to its medial and lateral sides, and therefore this augment may be used in either a right femur or a left femur.

As mentioned earlier, the present invention also relates to a set of femoral augments of different sizes, with a plurality of different heights being available for at least some of the sizes. In the preferred embodiment, a femoral augment is available for each size of femoral components, with a variety of heights available for each size. For example, Zimmer NexGen® femoral components, manufactured by Zimmer Inc. of Warsaw, Ind., are available in sizes designated as B, C, D, E and F, with B being the smallest size and F being the largest. If the femoral augments of the present invention were intended to be provided to cooperate with such femoral components, femoral augments would be provided in sizes designated as B, C, D, E and F, with several heights being available for each size. Each augment of such a system is configured to provide a gap between the augment posterior side and the inner posterior portion of the femoral component of between about 3.5 mm and about 5 mm, when the augment is implanted with a femoral component of a corresponding size designation (e.g., when a B-sized augment is implanted with a B-sized femoral component; a C-sized augment is implanted with a C-sized femoral component; etc.).

Continuing with the example of a set of femoral augments being provided for NexGen® femoral components, such a set preferably includes B-sized augments in 20 mm and 30 mm heights; C-sized augments in 20 mm and 30 mm heights; D-sized augments in 20 mm, 30 mm, 40 mm and 50 mm heights; E-sized augments in 20 mm, 30 mm, 40 mm and 50 mm heights; and F-sized augments in 22 mm, 30 mm, 40 mm and 50 mm heights. An F-sized augment in a 22 mm height is provided instead of a 20 mm height because the 20 mm height in this size would result in a web portion (such as web portion 36 in FIG. 7) of such a narrow thickness that breakage may result. Preferably, the 40 mm and the 50 mm height augments are provided in both right and left versions. However, as mentioned earlier, the 20 mm (or 22 mm) and the 30 mm height augments are symmetric with respect to the medial and lateral sides, so different right and left versions are not necessary.

Of course, the femoral augments of the present invention can be configured for use with essentially any type of femoral component from any manufacturer, and the examples provided are for the purposes of explanation only. Moreover, sizes and heights other than those mentioned above can be provided, whether being used in association with NexGen® femoral components or other femoral components. Additionally, it is also contemplated that due to the versatility of the femoral augments of the present invention, that augments manufactured for one brand or type of femoral component may also be used with another brand or type of femoral component.

Figure 8:
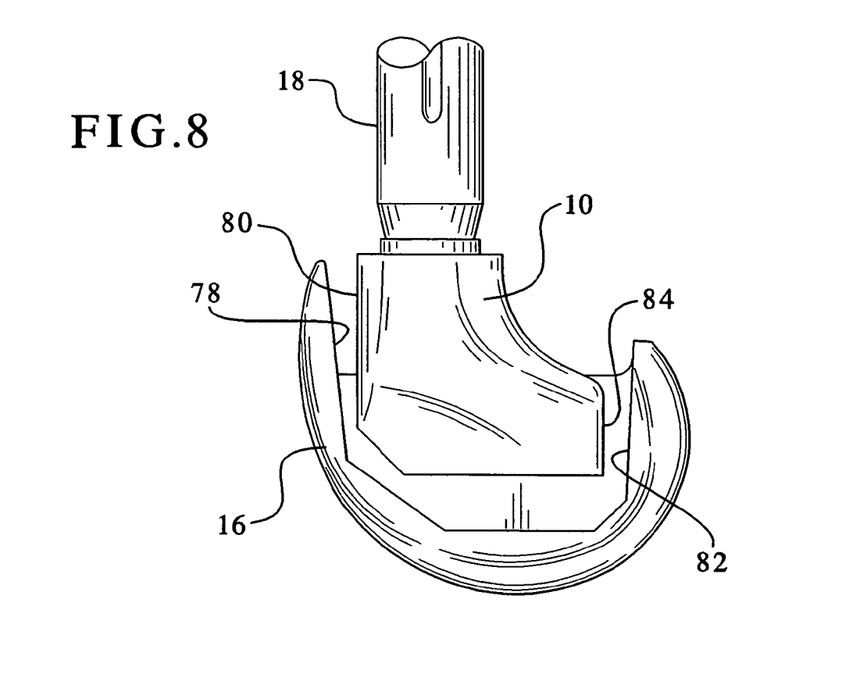
FIG. 8 is a side view of a femoral augment inserted into a femoral component of a corresponding size.
Figure 9:
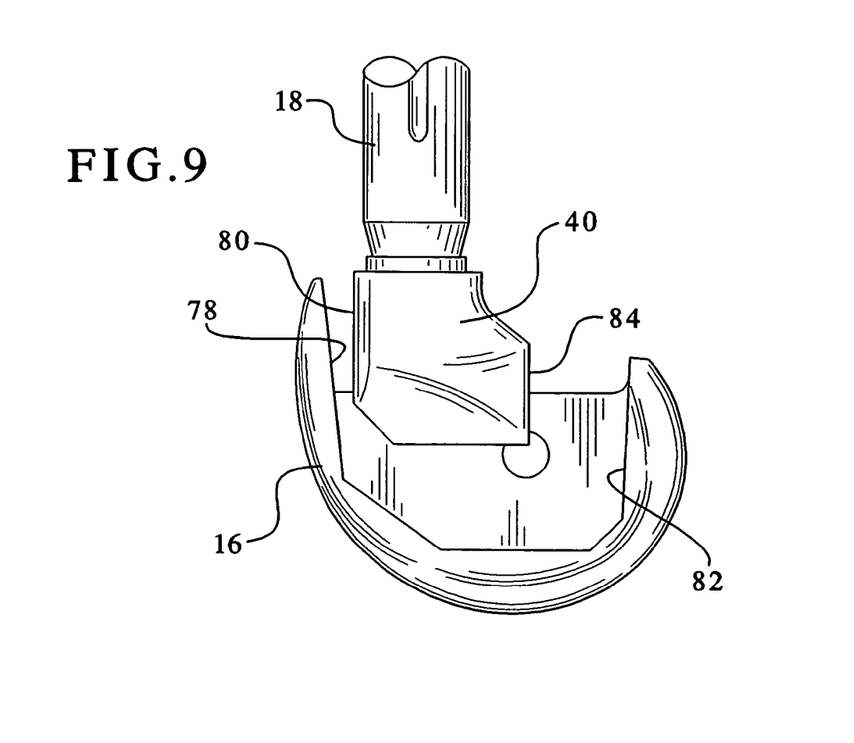
FIG. 9 is a side view of a femoral augment inserted into a femoral component that is of a size several levels larger than the femoral augment.

The versatility of the femoral augments of the present invention is also shown by the fact that, preferably, at least one of the femoral augments of the set can be used with femoral components of more than one different size. More preferably, each of the femoral augments within the set of femoral augments of the preferred embodiment, no matter what size or height, can preferably be used with any of the femoral components, no matter what size. For example, turning now to FIGS. 8 and 9, which show and refer to NexGen® femoral components, FIG. 8 shows a 50 mm height F-sized augment 10 positioned with a size F femoral component, and FIG. 9 shows a 20 mm height B-sized augment 40 positioned with a size F femoral component. As can be seen in these figures, although the anterior gap between the anterior inner wall 78 of femoral component 16 and the anterior exterior wall 80 of the augments is the same for augments 10 and 40 (of, respectively, FIGS. 8 and 9), the posterior gap between the posterior inner wall 82 of femoral component 16 and the posterior wall 84 of the augments 10 and 40 is different. In particular, the posterior gap of FIG. 9 is much greater than the posterior gap of FIG. 8, with the posterior gap in FIG. 9 being, for example, approximately 16 mm or more, and the gap in FIG. 8 being, for example, less than approximately 5 mm. In the preferred embodiment, all of the augments of a particular size can be utilized with, at least, all of the femoral components of that particular size and all larger sized femoral components. It is also contemplated that a set of augments could be provided in which all of the sizes and heights of femoral augments could be utilized with all of the sizes of femoral components. Such versatility provides the surgeon with flexibility when selecting the appropriate augment size and height so that it fits the defect size and height, regardless of the size of femoral component being used.

Preferably, each different size and height of femoral augment will also be available as a provisional. Provisional femoral augments, which will be referred to herein simply as provisionals, are temporary components used as a test to ensure that the permanent femoral augment will fit within the cavity in the femur. Although only one size provisional will be shown and described, provisional augments should be made to correspond to every size and height of femoral augment.

There are two main differences between the provisionals and the permanent femoral augments. First, provisional augments may be made of a material which indicates the bony areas of the provisional so that the surgeon can visualize how the augment fits within the cavity. For example, the provisional may be made of a transparent or photo-elastic material. One example of a suggested material for the provisional is polyphenylsulfone, although other materials are also contemplated.

Second, provisional augments preferably include one or more grooves, such as groove 86 found on leg 24 of FIG. 1 (a mirror image of groove 86 (not shown) may also be provided on leg 26). Groove 86 (and any associated groove) preferably extends in the generally anterior/posterior direction, and is configured to cooperate with a tool for removing the provisional from within the cavity, such as the tool shown in FIG. 10 and designated as provisional remover 90. Alternatively, a pair of grooves on the legs 24/26, like groove 86, could be configured for use with the adjustable provisional holder shown in FIGS. 10 and 11 of application Ser. No. 10/780,378, filed on Feb. 17, 2004, the contents of which are hereby incorporated by reference. Of course, the groove(s) may be omitted if another method of removing the provisionals from the cavity is utilized.

Figure 10:
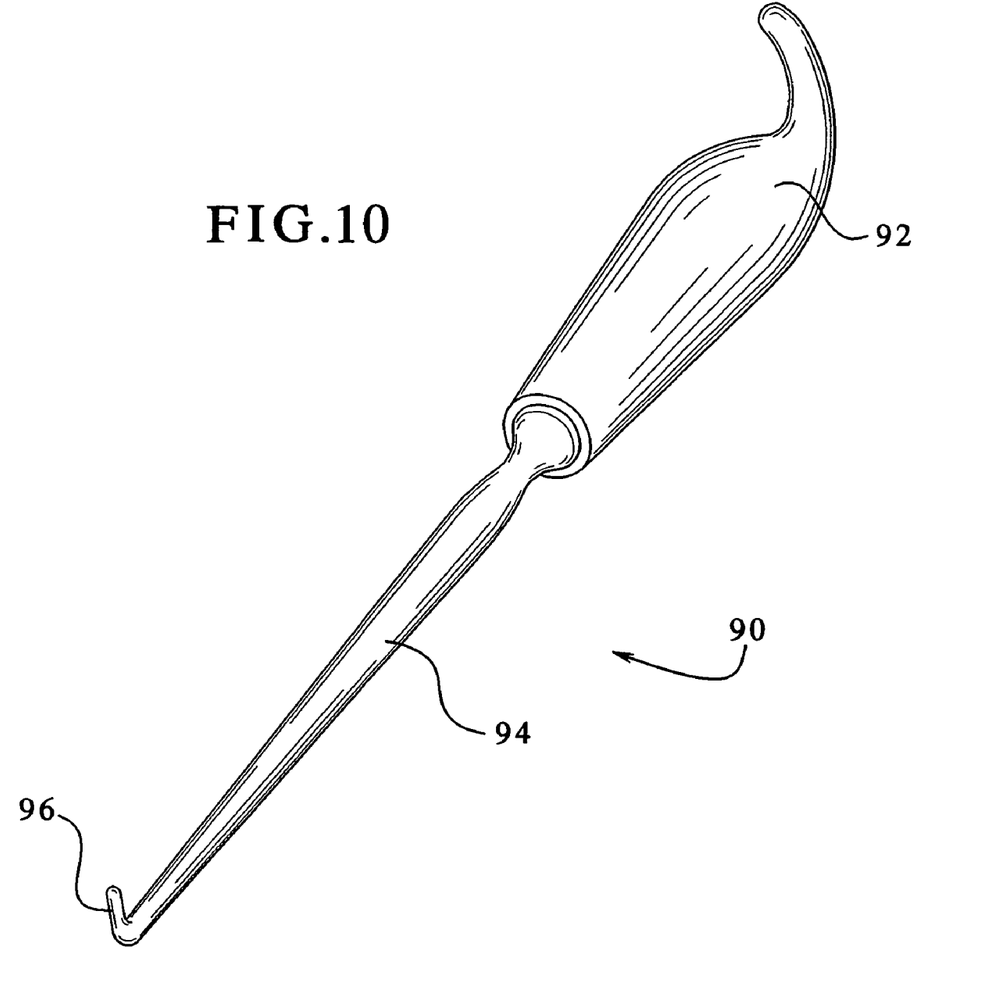
FIG. 10 is a perspective view of a provisional remover.

Turning now to FIG. 10, one embodiment of a provisional remover will be described. Remover 90 includes a handle 92 and a shaft 94, where the end of shaft 94 preferably includes a hook portion 96. Hook portion 96 may be straight, as shown, to define a generally "L" shape with shaft 94, or it may be curved. Preferably, the entire provisional remover 90 is made from stainless steel, although other materials, such as other metals or plastics, are also contemplated as suitable materials. Additionally, the handle 92 may be made of a different material from the shaft 94, if desired.

Figure 11:
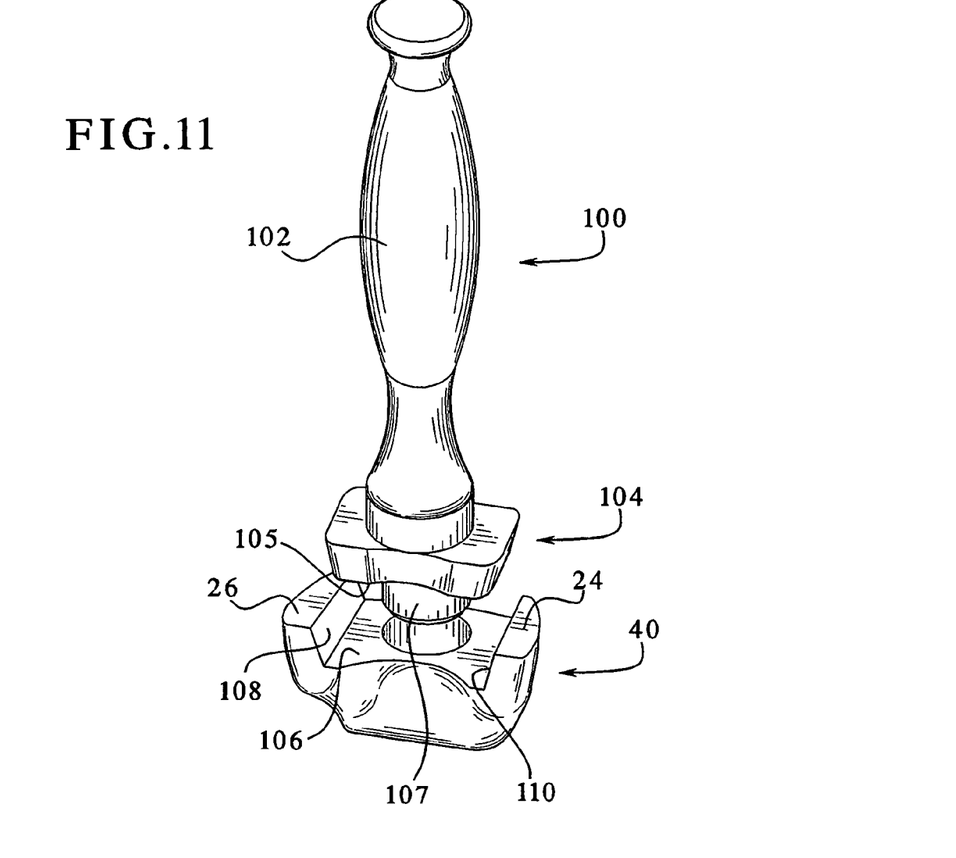
FIG. 11 is an exploded view of a pusher being inserted into a femoral augment.
Figure 12:
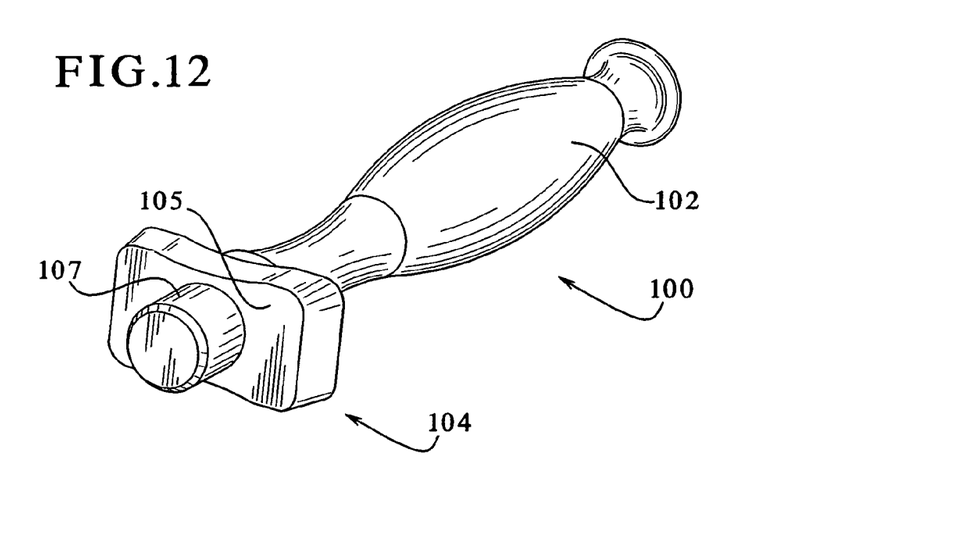
FIG. 12 is a perspective view of the pusher of FIG. 10.

Turning now to FIGS. 11 and 12, one embodiment of a pusher for implanting the femoral augments (and the provisionals) into the femur will be shown and described. More specifically, FIG. 11 shows pusher 100 aligned with femoral augment 40, and FIG. 12 shows a bottom perspective view of pusher 100. It should be noted that in order to provide better clarity, FIG. 11 is inverted from the normal orientation in which pusher 100 and femoral augment 40 will be positioned. In other words, in its normal positioning, augment 40 will be above pusher 100, so that pusher 100 can be used to push augment 40 upwardly into a femur.

The pusher 100 includes a handle portion 102 and an augment seating portion 104, which includes a generally planar surface 105 and generally cylindrical portion 107. The augment seating portion 104 is preferably shaped to complement the interior surfaces of the femoral augments 10, 20, 30 and 40, except in that the surfaces and configurations of augment seating portion 104 are slightly smaller than the corresponding surfaces of the femoral augments, which permits the augment seating portion 104 to be easily seated within (and easily withdrawn from) the femoral augments and the provisionals. The distal surface 106 of web portion 36 (FIG. 7) and the inner side surfaces 108, 110 of legs 26, 24 are preferably of the same size and shape for all sizes and heights of the femoral augments. Therefore, a single pusher 100 can be used with all of the femoral augments and provisionals of all of the different sizes and heights. Of course, if the relevant surfaces of the augments and provisionals of different sizes are configured to be of different sizes or shapes, multiple pushers with different seating portions can be provided.

In its preferred form, pusher 100 is preferably made with an aluminum handle portion 102 and an acetyl seating portion 104. However, other materials can also be used. For example, the seating portion could be made from various polymers or metals and the handle portion could be made of a different metal or from plastic.

A brief discussion of a method of utilizing the present invention will be provided next. If the surgeon for a knee joint replacement surgical technique determines that there is significant bone loss in the distal femur, the surgeon then determines whether a femoral augment of the present invention could be utilized to fill the void in the femur. If a femoral augment is to be used, the surgeon estimates the proper size and height of femoral augment to be used, and also estimates the intended implanted position of the femoral augment. The femoral augments of the present invention are preferably provided in a wide variety of sizes and heights, as discussed above, which should enable the surgeon to find an appropriate augment for filling a cavitary defect that will only require minor shaping of the defect, such as with a rasp or burr tool. Accordingly, only a minimal amount of healthy bone should need to be removed in order to prepare a cavity for receiving one of the femoral augments of the present invention.

Moreover, healthy bone removal is also minimized because the present femoral augments provide the surgeon with some flexibility with regard to the implantation location and orientation of the augment. For example, each of the present femoral augments may be positioned in any one location chosen from a range of locations that are at different distances from a femoral component. Further, as shown for example in FIG. 4, the present femoral augment may be offset with respect to the femoral component. Thus, with such versatility in implantation location, augment size and augment height being provided with the present invention, the surgeon should be able to select an augment size (regardless of the femoral component size), an augment height, an implanted location, and an implanted orientation that only requires minimal rasping or use of a burr tool to prepare a cavity for receiving the selected femoral augment.

After preparing the cavity for receiving a femoral augment, a provisional augment of the same size and height should be temporarily implanted to determine whether the cavity is properly sized, or if additional bone needs to be removed and/or if a different size and/or height augment needs to be selected. The appropriate size and height provisional may then be inserted into the cavity by using a pusher (such as pusher 100 of FIGS. 11 and 12), or by any other desired method. At this point, the provisional is also preferably used to trial the locations of the femoral component 16 and stem extension 18, as well as the location of any conventional distal augments being provided upon the femoral component. After the fit is adequately tested with the provisional, it can be removed by using the provisional remover 90 (shown in FIG. 10) or by any other desired technique. Then, the permanent femoral augment is inserted, such as by using the pusher 100, or by any other desired method. After properly seating the augment within the cavity, cement is applied to the inner cavity surfaces of the augment and the inner surface of femoral component 16. Next, the femoral component 16, with the stem extension attached thereto, is attached to the augment and to the peripheral bone remaining around the cavity. Then, the remainder of the knee joint prosthesis is attached using any desired method, and the surgical procedure continues in the customary manner.

While various embodiments of the present invention have been shown and described, it should be understood that other modifications, substitutions and alternatives may be apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. An implant system for use with a knee joint prosthesis, said system comprising:
   at least one femoral component of a knee joint prosthesis, each said at least one femoral component including a pair of condylar portions; and
   a plurality of femoral augments configured to be positioned proximal of said at least one femoral component, each said plurality of femoral augments including:
   a main body portion; and
   a pair of legs extending outwardly from said main body portion in a generally posterior direction, said pair of legs configured to be seated upon a proximal side of said pair of condylar portions of said at least one femoral component;
   wherein at least one of said plurality of femoral augments includes a proximal side of said main body portion that defines a relatively flat surface with a generally trapezoidal shape defined by a longer base section and a shorter base section that are connected by two leg sections; and
   wherein another of said plurality of femoral augments includes outer medial and lateral surfaces of said main body portion that are tapered inwardly towards a proximal direction to define a generally conical portion of a generally quadrilateral-shaped cross-section with a truncated proximal surface.

2. The implant system defined in claim 1, further comprising a pusher configured and arranged for implanting one of said plurality of femoral augments into a distal portion of a femur.

3. The implant system defined in claim 1, further comprising at least one provisional femoral augment corresponding in shape and size to at least one of said plurality of femoral augments.

4. The implant system defined in claim 3, further comprising:
   at least one groove on an inner surface of said at least one provisional femoral augment; and
   a provisional remover configured to cooperate with said at least one groove for removal of said provisional femoral augment from an implanted position.

5. The implant system defined in claim 1, wherein said at least one femoral component includes a plurality of femoral components of different sizes, and further wherein said plurality of femoral augments is adapted for use with femoral components of more than one different size.

6. The implant system defined in claim 1, wherein:
   said at least one femoral component includes a plurality of femoral components of different sizes; and
   said plurality of femoral augments includes femoral augments of different sizes, with each of said different sizes including differences in medial/lateral dimensions and/or differences in anterior/posterior dimensions, and further wherein femoral augments of multiple distal/proximal heights are provided for at least some of said different sizes.

7. The implant system defined in claim 1, wherein at least one of said plurality of femoral augments is configured and arranged to allow positioning in an offset or tilted location with respect to said femoral component, in order to maximize contact with remaining endosteal bone of the distal femur.

8. A set of femoral augments for use with a knee joint prosthesis, said set comprising a plurality of femoral augments, of a plurality of different sizes, wherein each of said femoral augments comprises:
   a main body portion; and
   a pair of legs extending outwardly from said main body portion in a generally posterior direction, said pair of legs configured to be seated upon a proximal side of a pair of condylar portions of a femoral component, wherein:
   at least one of said femoral augments is symmetrical, with respect to its lateral and medial sides, thereby allowing implantation into either a right femur or a left femur;
   at least one of said femoral augments is asymmetrical, with respect to its lateral and medial sides, thereby limiting its implantation location to a right femur; and
   at least one of said femoral augments is asymmetrical, with respect to its lateral and medial sides, thereby limiting its implantation location to a left femur.

* * * * *